United States Patent
Van Melderen et al.

(10) Patent No.: US 10,696,997 B2
(45) Date of Patent: Jun. 30, 2020

(54) METHOD AND SYSTEM FOR THE PRODUCTION OF RECOMBINANT PROTEINS BY CELLS

(71) Applicant: UNIVERSITE LIBRE DE BRUXELLES, Brussels (BE)

(72) Inventors: Laurence Van Melderen, Waterloo (BE); Baptiste J. S. Dumont, Brussels (BE); Thibaut Hallaert, Waterloo (BE); Gilles Vanwalleghem, Rhode st Genèse (BE); Philippe Goffin, Louvain-la-Neuve (BE)

(73) Assignee: UNIVERSITE LIBRE DE BRUXELLES, Brussels (BE)

( * ) Notice: Subject to any disclaimer, the term of this patent is extended or adjusted under 35 U.S.C. 154(b) by 29 days.

(21) Appl. No.: 15/323,891

(22) PCT Filed: Jul. 6, 2015

(86) PCT No.: PCT/EP2015/065350
§ 371 (c)(1),
(2) Date: Jan. 4, 2017

(87) PCT Pub. No.: WO2016/001447
PCT Pub. Date: Jan. 7, 2016

(65) Prior Publication Data
US 2017/0314053 A1 Nov. 2, 2017

(30) Foreign Application Priority Data
Jul. 4, 2014 (EP) .................. PCT/EP2014/064355

(51) Int. Cl.
| | | |
|---|---|---|
| *C12N 15/65* | (2006.01) | |
| *C12P 21/02* | (2006.01) | |
| *C12N 15/70* | (2006.01) | |
| *C12N 15/10* | (2006.01) | |
| *C12N 15/66* | (2006.01) | |
| *C07K 14/245* | (2006.01) | |
| *C07K 14/435* | (2006.01) | |
| *C12N 15/81* | (2006.01) | |

(52) U.S. Cl.
CPC ............ *C12P 21/02* (2013.01); *C07K 14/245* (2013.01); *C07K 14/43595* (2013.01); *C12N 15/10* (2013.01); *C12N 15/65* (2013.01); *C12N 15/66* (2013.01); *C12N 15/70* (2013.01); *C12N 15/81* (2013.01); *C07K 2319/50* (2013.01); *C07K 2319/60* (2013.01); *C07K 2319/92* (2013.01)

(58) Field of Classification Search
CPC .................................................... C12N 15/65
See application file for complete search history.

(56) References Cited

FOREIGN PATENT DOCUMENTS

| WO | 03/078638 A1 | 9/2003 |
|---|---|---|
| WO | 2004/0022745 A2 | 3/2004 |
| WO | 2007/0109781 A2 | 9/2007 |
| WO | 2012/038950 A1 | 3/2012 |

OTHER PUBLICATIONS

Schiott et al. 2000; Efficient spore synthesis in Bascillus subtillis depends on the CcdA protein. J. Bacteriol. 182(10): 2845-2854.*
Zhang et al. 2003; Characterization of the interactions within the mazEF addiction module of *Escherichia coli*. J. Bio. Chem. 278(34): 32300-32306.*
International Search Report and Written Opinion for corresponding International Patent Application No. PCT/EP2015/065350, dated Oct. 14, 2015.
Kromer Wolfgang J et al: "Expression of the membrane protein glycophorin A as a fusion with the antibiotic resistance protein neomycin phosphotransferase II", Biotechnology and Bio Engineering, Wiley & Sons, Hoboken, NJ, US, vol. 57, No. 2, Jan. 20, 1998 (Jan. 20, 1998), pp. 238-244, XP002383206.
Aliona Bogdanova et al: "Is the fusion of an antibiotic resistance protein with another protein functional?", ResearchGate, Dec. 19, 2012 (Dec. 19, 2012), XP055215049. Retrieved from the Internet: URL:http://www.researchgate.net/post/Is_the_fusion_of_an_antibiotic_resistance_pratein_with_another_protein_functional [retrieved on Sep. 22, 2015].
J.-H. Park et al: "Intramolecular Regulation of the Sequence-Specific mRNA Interferase Activity of MazF Fused to a MazE Fragment with a Linker Cleavable by Specific Proteases", Applied and Environmental Microbiology, vol. 78, No. 11, Jun. 1, 2012 (Jun. 1, 2012), pp. 3794-3799, XP055113738.
Wu Dai-Tze et al: "MLV based viral-like-particles for delivery of toxic proteins and nuclear transcription factors", Biomaterials, vol. 35, No. 29, Jul. 3, 2014 (Jul. 3, 2014), pp. 8416-8426, XP028880170.
Assaf Shapira et al: "Removal of Hepatitis C Virus-Infected Cells by a Zymogenized Bacterial Toxin", PLOS ONE, vol . 7, No. 2, Feb. 16, 2012 (Feb. 16, 2012), p. e32320, XP055215551.
K. Nehlsen et al: "Toxin-antitoxin based transgene expression in mammalian cells", Nucleic Acids Research, vol . 38, No. 5, Dec. 8, 2009 (Dec. 8, 2009), pp. e32-e32, XP055021115.
Ekaterina Minskaia et al: "Protein Coexpression Using FMDV 2A: Effect of "Linker" Residues", Biomed Research International, vol . 66, No. 5, Jan. 1, 2013 (Jan. 1, 2013), pp. 41-12, XP055215236.
Colin W. Dykes et al: "Expression of atrial natriuretic factor as a cleavable fusion protein with chloramphenicol acetyltransferase in *Escherichia coli*", European Journal of Biochemistry, vol. 174, No. 2, Jun. 1, 1988 (Jun. 1, 1988), pp. 411-416, XP055215322.

(Continued)

*Primary Examiner* — Karen Cochrane Carlson
(74) *Attorney, Agent, or Firm* — Merchant & Gould P.C.

(57) ABSTRACT

A cassette sequence for the transformation of a host cell includes at least: a first nucleotide sequence encoding a peptide or protein of interest to be produced by the host cell. The first sequence is linked to a second nucleotide sequence providing resistance to a toxin or encoding an antitoxin peptide to the toxin. The nucleotide sequences are organized in such a way that production of the peptide encoded by the second nucleotide sequence(s) is translationally coupled to production of the peptide encoded by the first nucleotide sequence.

14 Claims, 3 Drawing Sheets

Specification includes a Sequence Listing.

(56) References Cited

OTHER PUBLICATIONS

Xiaoying Chen et al: "Fusion protein linkers: Property, design and functionality", Advanced Drug Delivery Reviews, Sep. 1, 2012 (Sep. 1, 2012), XP055062583.

Elizabeth Di Ago-Navarro et al: "parD toxin-antitoxin system of plasmid RI-basic contributions, biotechnological applications and relationships with closely-related toxin-antitoxin systems", FEBS Journal, vol . 277, No. 15, Aug. 21, 2010 (Aug. 21, 2010), pp. 3097-3117, XP055214885.

Anonymous: "StabyExpress T7 kit Manual (v2.0)", Feb. 18, 2014 (Feb. 18, 2014), XP055214888.

Szpirer Cedric Y et al: "Separate-component-stabilization system for protein and DNA production without the use of antibiotics", Biotechniques, Informa Healthcare, US, vol. 38, No. 5, May 1, 2005 (May 1, 2005), pp. 175-781, XP001538926.

Stieber D et al: "The art of selective killing: plasmid toxin/antitoxin systems and their technological applications", Biotechniques, Informa Healthcare, US, vol . 45, No. 3, Sep. 1, 2008 (Sep. 1, 2008), pp. 344-346, XP002734891.

Cueva-Mendez et al: "Biotechnological and Medical Exploitations of Toxin-Antitoxin Genes and Their Components", Prokaryotic Toxin-Antitoxins, Edited by Kenn Gerdes, Jan. 1, 2013 (Jan. 1, 2013), pp. 341-360, XP009186154.

Barbara Kedzierska et al., "Toxin—antitoxin regulation: bimodal interaction of YefM—YoeB with paired DNA palindromes exerts transcriptional autorepression", Nucleic Acids Research, vol. 35, No. 1, p. 325-339 (2007).

Office Action from European Patent Application No. 15744489.4, dated Apr. 10, 2018.

* cited by examiner

SEQ ID NO: 1 - APOL1 sequence with V5 and 6His-tag:

MEGAALLRVSVLCIWMSALFLGVGVRAEEAGARVQQNVPSGTDTGDPQSKPLGDWAAGT
MDPESSIFIEDAIKYFKEKVSIQNLLLLLTDNEAWNGFVAAAELPRNEADELRKALDNLARQMI
MKDKNWHDKGQQYRNWFLKEFPRLKSKLEDNIRRLRALADGVQKVHKGTTIANVVSGSLSI
SSGILTLVGMGLAPFTEGGSLVLLEPGMELGITAALTGITSSTIDYGKKWWTQAQAHDLVIKS
LDKLKEVKEFLGENISNFLSLAGNTYQLTRGIGKDIRALRRARANLQSVPHASASRPRVTEPI
SAESGEQVERVNEPSILEMSRGVKLTDVAPVSFFLVLDVVYLVYESKHLHEGAKSETAEELK
KVAQELEEKLNILNNNYKILQADQELLESRGPFEGKPIPNPLLGLDSTRTGHHHHHH

SEQ ID NO: 2 - 2A peptide:

GSGATNFSLLKQAGDVEENPGP

SEQ ID NO: 3 - Antitoxin sequence (CcdA):

MKQRITVTVDSDSYQLLKAYDVNISGLVSTTMQNEARRLRAERWKAENQEGMAEVARFIEM
NGSFADENRDW

SEQ ID NO:4

MEGAALLRVSVLCIWMSALFLGVGVRAEEAGARVQQNVPSGTDTGDPQSKPLGDWAAGT
MDPESSIFIEDAIKYFKEKVSIQNLLLLLTDNEAWNGFVAAAELPRNEADELRKALDNLARQMI
MKDKNWHDKGQQYRNWFLKEFPRLKSKLEDNIRRLRALADGVQKVHKGTTIANVVSGSLSI
SSGILTLVGMGLAPFTEGGSLVLLEPGMELGITAALTGITSSTIDYGKKWWTQAQAHDLVIKS
LDKLKEVKEFLGENISNFLSLAGNTYQLTRGIGKDIRALRRARANLQSVPHASASRPRVTEPI
SAESGEQVERVNEPSILEMSRGVKLTDVAPVSFFLVLDVVYLVYESKHLHEGAKSETAEELK
KVAQELEEKLNILNNNYKILQADQELLESRGPFEGKPIPNPLLGLDSTRTGHHHHHHGSGAT
NFSLLKQAGDVEENPGPMKQRITVTVDSDSYQLLKAYDVNISGLVSTTMQNEARRLRAERW
KAENQEGMAEVARFIEMNGSFADENRDW

SEQ ID NO:5
MEGAALLRVSVLCIWMSALFLGVGVRAEEAGARVQQNVPSGTDTGDPQSKPLGDWAAGT
MDPESSIFIEDAIKYFKEKVSIQNLLLLLTDNEAWNGFVAAAELPRNEADELRKALDNLARQMI
MKDKNWHDKGQQYRNWFLKEFPRLKSKLEDNIRRLRALADGVQKVHKGTTIANVVSGSLSI
SSGILTLVGMGLAPFTEGGSLVLLEPGMELGITAALTGITSSTIDYGKKWWTQAQAHDLVIKS
LDKLKEVKEFLGENISNFLSLAGNTYQLTRGIGKDIRALRRARANLQSVPHASASRPRVTEPI
SAESGEQVERVNEPSILEMSRGVKLTDVAPVSFFLVLDVVYLVYESKHLHEGAKSETAEELK
KVAQELEEKLNILNNNYKILQADQELLESRGPFEGKPIPNPLLGLDSTRTGHHHHHHGSGAT
NFSLLKQAGDVEENP

SEQ ID NO:6

PMKQRITVTVDSDSYQLLKAYDVNISGLVSTTMQNEARRLRAERWKAENQEGMAEVARFIE
MNGSFADENRDW

FIG. 2A

SEQUENCE LISTING

<160> NUMBER OF SEQ ID NOS: 16

<210> SEQ ID NO 1
<211> LENGTH: 429
<212> TYPE: PRT
<213> ORGANISM: Unknown
<220> FEATURE:
<223> OTHER INFORMATION: HUMAN APOL-1 sequence

<400> SEQUENCE: 1

Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
            20                  25                  30

Arg Val Gln Gln Asn Val Pro Ser Gly Thr Asp Thr Gly Asp Pro Gln
        35                  40                  45

Ser Lys Pro Leu Gly Asp Trp Ala Ala Gly Thr Met Asp Pro Glu Ser
    50                  55                  60

Ser Ile Phe Ile Glu Asp Ala Ile Lys Tyr Phe Lys Glu Lys Val Ser
65                  70                  75                  80

Ile Gln Asn Leu Leu Leu Leu Thr Asp Asn Glu Ala Trp Asn Gly
                85                  90                  95

Phe Val Ala Ala Ala Glu Leu Pro Arg Asn Glu Ala Asp Glu Leu Arg
            100                 105                 110

Lys Ala Leu Asp Asn Leu Ala Arg Gln Met Ile Met Lys Asp Lys Asn
        115                 120                 125

Trp His Asp Lys Gly Gln Gln Tyr Arg Asn Trp Phe Leu Lys Glu Phe
    130                 135                 140

Pro Arg Leu Lys Ser Lys Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
    210                 215                 220

```
Ser Ser Thr Ile Asp Tyr Gly Lys Lys Trp Trp Thr Gln Ala Gln Ala
225                 230                 235                 240

His Asp Leu Val Ile Lys Ser Leu Asp Lys Leu Lys Glu Val Lys Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
        275                 280                 285

Ala Arg Ala Asn Leu Gln Ser Val Pro His Ala Ser Ala Ser Arg Pro
    290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu
            340                 345                 350

Val Tyr Glu Ser Lys His Leu His Glu Gly Ala Lys Ser Glu Thr Ala
        355                 360                 365

Glu Glu Leu Lys Lys Val Ala Gln Glu Leu Glu Lys Leu Asn Ile
370                 375                 380

Leu Asn Asn Tyr Lys Ile Leu Gln Ala Asp Gln Glu Leu Leu Glu
385                 390                 395                 400

Ser Arg Gly Pro Phe Glu Gly Lys Pro Ile Pro Asn Pro Leu Leu Gly
            405                 410                 415

Leu Asp Ser Thr Arg Thr Gly His His His His His His
            420                 425

<210> SEQ ID NO 2
<211> LENGTH: 22
<212> TYPE: PRT
<213> ORGANISM: Unknown
<220> FEATURE:
<223> OTHER INFORMATION: VIRAL sequence presumed to be derived from Foot
      and Mouth Disease

<400> SEQUENCE: 2

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 3
<211> LENGTH: 72
<212> TYPE: PRT
<213> ORGANISM: Unknown
<220> FEATURE:
<223> OTHER INFORMATION: anti-toxin sequence (CcdA) isolated from
      E. coli

<400> SEQUENCE: 3

Met Lys Gln Arg Ile Thr Val Thr Val Asp Ser Asp Ser Tyr Gln Leu
1               5                   10                  15

Leu Lys Ala Tyr Asp Val Asn Ile Ser Gly Leu Val Ser Thr Thr Met
            20                  25                  30

Gln Asn Glu Ala Arg Arg Leu Arg Ala Glu Arg Trp Lys Ala Glu Asn
        35                  40                  45

Gln Glu Gly Met Ala Glu Val Ala Arg Phe Ile Glu Met Asn Gly Ser
    50                  55                  60
```

```
Phe Ala Asp Glu Asn Arg Asp Trp
 65                  70

<210> SEQ ID NO 4
<211> LENGTH: 523
<212> TYPE: PRT
<213> ORGANISM: Unknown
<220> FEATURE:
<223> OTHER INFORMATION: HUMAN APOL-1 sequence

<400> SEQUENCE: 4

Met Glu Gly Ala Ala Leu Leu Arg Val Ser Val Leu Cys Ile Trp Met
 1               5                  10                  15

Ser Ala Leu Phe Leu Gly Val Gly Val Arg Ala Glu Glu Ala Gly Ala
                20                  25                  30

Arg Val Gln Gln Asn Val Pro Ser Gly Thr Asp Thr Gly Asp Pro Gln
             35                  40                  45

Ser Lys Pro Leu Gly Asp Trp Ala Ala Gly Thr Met Asp Pro Glu Ser
 50                  55                  60

Ser Ile Phe Ile Glu Asp Ala Ile Lys Tyr Phe Lys Glu Lys Val Ser
 65                  70                  75                  80

Ile Gln Asn Leu Leu Leu Leu Thr Asp Asn Glu Ala Trp Asn Gly
                 85                  90                  95

Phe Val Ala Ala Ala Glu Leu Pro Arg Asn Glu Ala Asp Glu Leu Arg
                100                 105                 110

Lys Ala Leu Asp Asn Leu Ala Arg Gln Met Ile Met Lys Asp Lys Asn
            115                 120                 125

Trp His Asp Lys Gly Gln Gln Tyr Arg Asn Trp Phe Leu Lys Glu Phe
        130                 135                 140

Pro Arg Leu Lys Ser Lys Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
210                 215                 220

Ser Ser Thr Ile Asp Tyr Gly Lys Lys Trp Trp Thr Gln Ala Gln Ala
225                 230                 235                 240

His Asp Leu Val Ile Lys Ser Leu Asp Lys Leu Lys Glu Val Lys Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
        275                 280                 285

Ala Arg Ala Asn Leu Gln Ser Val Pro His Ala Ser Ala Ser Arg Pro
    290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu
            340                 345                 350
```

```
Val Tyr Glu Ser Lys His Leu His Glu Gly Ala Lys Ser Glu Thr Ala
        355                 360                 365

Glu Glu Leu Lys Lys Val Ala Gln Glu Leu Glu Lys Leu Asn Ile
370                 375                 380

Leu Asn Asn Asn Tyr Lys Ile Leu Gln Ala Asp Gln Glu Leu Leu Glu
385                 390                 395                 400

Ser Arg Gly Pro Phe Glu Gly Lys Pro Ile Pro Asn Pro Leu Leu Gly
                405                 410                 415

Leu Asp Ser Thr Arg Thr Gly His His His His His Gly Ser Gly
                420                 425                 430

Ala Thr Asn Phe Ser Leu Leu Lys Gln Ala Gly Asp Val Glu Glu Asn
                435                 440                 445

Pro Gly Pro Met Lys Gln Arg Ile Thr Val Thr Val Asp Ser Asp Ser
                450                 455                 460

Tyr Gln Leu Leu Lys Ala Tyr Asp Val Asn Ile Ser Gly Leu Val Ser
465                 470                 475                 480

Thr Thr Met Gln Asn Glu Ala Arg Arg Leu Arg Ala Glu Arg Trp Lys
                    485                 490                 495

Ala Glu Asn Gln Glu Gly Met Ala Glu Val Ala Arg Phe Ile Glu Met
                500                 505                 510

Asn Gly Ser Phe Ala Asp Glu Asn Arg Asp Trp
            515                 520

<210> SEQ ID NO 5
<211> LENGTH: 449
<212> TYPE: PRT
<213> ORGANISM: Unknown
<220> FEATURE:
<223> OTHER INFORMATION: HUMAN APOL-1 sequence

<400> SEQUENCE: 5

Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
                20                  25                  30

Arg Val Gln Gln Asn Val Pro Ser Gly Thr Asp Thr Gly Asp Pro Gln
            35                  40                  45

Ser Lys Pro Leu Gly Asp Trp Ala Ala Gly Thr Met Asp Pro Glu Ser
    50                  55                  60

Ser Ile Phe Ile Glu Asp Ala Ile Lys Tyr Phe Lys Glu Lys Val Ser
65                  70                  75                  80

Ile Gln Asn Leu Leu Leu Leu Thr Asp Asn Glu Ala Trp Asn Gly
                85                  90                  95

Phe Val Ala Ala Ala Glu Leu Pro Arg Asn Glu Ala Asp Glu Leu Arg
                100                 105                 110

Lys Ala Leu Asp Asn Leu Ala Arg Gln Met Ile Met Lys Asp Lys Asn
                115                 120                 125

Trp His Asp Lys Gly Gln Gln Tyr Arg Asn Trp Phe Leu Lys Glu Phe
        130                 135                 140

Pro Arg Leu Lys Ser Lys Leu Glu Asp Asn Ile Arg Arg Leu Arg Ala
145                 150                 155                 160

Leu Ala Asp Gly Val Gln Lys Val His Lys Gly Thr Thr Ile Ala Asn
                    165                 170                 175

Val Val Ser Gly Ser Leu Ser Ile Ser Ser Gly Ile Leu Thr Leu Val
                180                 185                 190
```

```
Gly Met Gly Leu Ala Pro Phe Thr Glu Gly Gly Ser Leu Val Leu Leu
            195                 200                 205

Glu Pro Gly Met Glu Leu Gly Ile Thr Ala Ala Leu Thr Gly Ile Thr
210                 215                 220

Ser Ser Thr Ile Asp Tyr Gly Lys Lys Trp Trp Thr Gln Ala Gln Ala
225                 230                 235                 240

His Asp Leu Val Ile Lys Ser Leu Asp Lys Leu Lys Glu Val Lys Glu
            245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
            275                 280                 285

Ala Arg Ala Asn Leu Gln Ser Val Pro His Ala Ser Ala Ser Arg Pro
            290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
            325                 330                 335

Asp Val Ala Pro Val Ser Phe Phe Leu Val Leu Asp Val Val Tyr Leu
            340                 345                 350

Val Tyr Glu Ser Lys His Leu His Glu Gly Ala Lys Ser Glu Thr Ala
            355                 360                 365

Glu Glu Leu Lys Lys Val Ala Gln Glu Leu Glu Lys Leu Asn Ile
            370                 375                 380

Leu Asn Asn Asn Tyr Lys Ile Leu Gln Ala Asp Gln Glu Leu Leu Glu
385                 390                 395                 400

Ser Arg Gly Pro Phe Glu Gly Lys Pro Ile Pro Asn Pro Leu Leu Gly
                    405                 410                 415

Leu Asp Ser Thr Arg Thr Gly His His His His His His Gly Ser Gly
                    420                 425                 430

Ala Thr Asn Phe Ser Leu Leu Lys Gln Ala Gly Asp Val Glu Glu Asn
            435                 440                 445

Pro

<210> SEQ ID NO 6
<211> LENGTH: 73
<212> TYPE: PRT
<213> ORGANISM: Unknown
<220> FEATURE:
<223> OTHER INFORMATION: HUMAN APOL-1 sequence

<400> SEQUENCE: 6

Pro Met Lys Gln Arg Ile Thr Val Thr Val Asp Ser Asp Ser Tyr Gln
1               5                   10                  15

Leu Leu Lys Ala Tyr Asp Val Asn Ile Ser Gly Leu Val Ser Thr Thr
                20                  25                  30

Met Gln Asn Glu Ala Arg Arg Leu Arg Ala Glu Arg Trp Lys Ala Glu
            35                  40                  45

Asn Gln Glu Gly Met Ala Glu Val Ala Arg Phe Ile Glu Met Asn Gly
        50                  55                  60

Ser Phe Ala Asp Glu Asn Arg Asp Trp
65                  70

<210> SEQ ID NO 7
<211> LENGTH: 429
```

```
<212> TYPE: PRT
<213> ORGANISM: Unknown
<220> FEATURE:
<223> OTHER INFORMATION: HUMAN APOL-1 sequence

<400> SEQUENCE: 7

Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
            20                  25                  30

Arg Val Gln Gln Asn Val Pro Ser Gly Thr Asp Thr Gly Asp Pro Gln
        35                  40                  45

Ser Lys Pro Leu Gly Asp Trp Ala Ala Gly Thr Met Asp Pro Glu Ser
50                  55                  60

Ser Ile Phe Ile Glu Asp Ala Ile Lys Tyr Phe Lys Glu Lys Val Ser
65                  70                  75                  80

Ile Gln Asn Leu Leu Leu Leu Thr Asp Asn Glu Ala Trp Asn Gly
                85                  90                  95

Phe Val Ala Ala Ala Glu Leu Pro Arg Asn Glu Ala Asp Glu Leu Arg
            100                 105                 110

Lys Ala Leu Asp Asn Leu Ala Arg Gln Met Ile Met Lys Asp Lys Asn
        115                 120                 125

Trp His Asp Lys Gly Gln Gln Tyr Arg Asn Trp Phe Leu Lys Glu Phe
    130                 135                 140

Pro Arg Leu Lys Ser Lys Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
210                 215                 220

Ser Ser Thr Ile Asp Tyr Gly Lys Lys Trp Trp Thr Gln Ala Gln Ala
225                 230                 235                 240

His Asp Leu Val Ile Lys Ser Leu Asp Lys Leu Lys Glu Val Lys Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
        275                 280                 285

Ala Arg Ala Asn Leu Gln Ser Val Pro His Ala Ser Ala Ser Arg Pro
290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu
            340                 345                 350

Val Tyr Glu Ser Lys His Leu His Glu Gly Ala Lys Ser Glu Thr Ala
        355                 360                 365

Glu Glu Leu Lys Lys Val Ala Gln Glu Leu Glu Glu Lys Leu Asn Ile
370                 375                 380
```

```
Leu Asn Asn Asn Tyr Lys Ile Leu Gln Ala Asp Gln Glu Leu Leu Glu
385                 390                 395                 400

Ser Arg Gly Pro Phe Glu Gly Lys Pro Ile Pro Asn Pro Leu Leu Gly
                405                 410                 415

Leu Asp Ser Thr Arg Thr Gly His His His His His His
                420                 425

<210> SEQ ID NO 8
<211> LENGTH: 22
<212> TYPE: PRT
<213> ORGANISM: Unknown
<220> FEATURE:
<223> OTHER INFORMATION: VIRAL sequence presumed to be derived from Foot
      and Mouth Disease

<400> SEQUENCE: 8

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 9
<211> LENGTH: 72
<212> TYPE: PRT
<213> ORGANISM: Unknown
<220> FEATURE:
<223> OTHER INFORMATION: anti-toxin sequence (CcdA) isolated from
      E. coli

<400> SEQUENCE: 9

Met Lys Gln Arg Ile Thr Val Thr Val Asp Ser Asp Ser Tyr Gln Leu
1               5                   10                  15

Leu Lys Ala Tyr Asp Val Asn Ile Ser Gly Leu Val Ser Thr Thr Met
                20                  25                  30

Gln Asn Glu Ala Arg Arg Leu Arg Ala Glu Arg Trp Lys Ala Glu Asn
            35                  40                  45

Gln Glu Gly Met Ala Glu Val Ala Arg Phe Ile Glu Met Asn Gly Ser
        50                  55                  60

Phe Ala Asp Glu Asn Arg Asp Trp
65                  70

<210> SEQ ID NO 10
<211> LENGTH: 523
<212> TYPE: PRT
<213> ORGANISM: Unknown
<220> FEATURE:
<223> OTHER INFORMATION: artificial constructs of Human, viral and
      E-coli Origin

<400> SEQUENCE: 10

Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
                20                  25                  30

Arg Val Gln Gln Asn Val Pro Ser Gly Thr Asp Thr Gly Asp Pro Gln
            35                  40                  45

Ser Lys Pro Leu Gly Asp Trp Ala Ala Gly Thr Met Asp Pro Glu Ser
        50                  55                  60

Ser Ile Phe Ile Glu Asp Ala Ile Lys Tyr Phe Lys Glu Lys Val Ser
65                  70                  75                  80

Ile Gln Asn Leu Leu Leu Leu Leu Thr Asp Asn Glu Ala Trp Asn Gly
```

```
            85                  90                  95
Phe Val Ala Ala Ala Glu Leu Pro Arg Asn Glu Ala Asp Glu Leu Arg
            100                 105                 110

Lys Ala Leu Asp Asn Leu Ala Arg Gln Met Ile Met Lys Asp Lys Asn
            115                 120                 125

Trp His Asp Lys Gly Gln Gln Tyr Arg Asn Trp Phe Leu Lys Glu Phe
            130                 135             140

Pro Arg Leu Lys Ser Lys Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
            195                 200                 205

Glu Pro Gly Met Glu Leu Gly Ile Thr Ala Ala Leu Thr Gly Ile Thr
        210                 215                 220

Ser Ser Thr Ile Asp Tyr Gly Lys Lys Trp Trp Thr Gln Ala Gln Ala
225                 230                 235                 240

His Asp Leu Val Ile Lys Ser Leu Asp Lys Leu Lys Glu Val Lys Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
        275                 280                 285

Ala Arg Ala Asn Leu Gln Ser Val Pro His Ala Ser Ala Ser Arg Pro
        290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu
            340                 345                 350

Val Tyr Glu Ser Lys His Leu His Glu Gly Ala Lys Ser Glu Thr Ala
        355                 360                 365

Glu Glu Leu Lys Lys Val Ala Gln Glu Leu Glu Lys Leu Asn Ile
        370                 375                 380

Leu Asn Asn Asn Tyr Lys Ile Leu Gln Ala Asp Gln Glu Leu Leu Glu
385                 390                 395                 400

Ser Arg Gly Pro Phe Glu Gly Lys Pro Ile Pro Asn Pro Leu Leu Gly
            405                 410                 415

Leu Asp Ser Thr Arg Thr Gly His His His His His Gly Ser Gly
                420                 425                 430

Ala Thr Asn Phe Ser Leu Leu Lys Gln Ala Gly Asp Val Glu Glu Asn
            435                 440                 445

Pro Gly Pro Met Lys Gln Arg Ile Thr Val Thr Val Asp Ser Asp Ser
        450                 455                 460

Tyr Gln Leu Leu Lys Ala Tyr Asp Val Asn Ile Ser Gly Leu Val Ser
465                 470                 475                 480

Thr Thr Met Gln Asn Glu Ala Arg Arg Leu Arg Ala Glu Arg Trp Lys
                485                 490                 495

Ala Glu Asn Gln Glu Gly Met Ala Glu Val Ala Arg Phe Ile Glu Met
            500                 505                 510
```

Asn Gly Ser Phe Ala Asp Glu Asn Arg Asp Trp
        515                 520

<210> SEQ ID NO 11
<211> LENGTH: 449
<212> TYPE: PRT
<213> ORGANISM: Unknown
<220> FEATURE:
<223> OTHER INFORMATION: artificial constructs of Human, viral and
      E-coli Origin

<400> SEQUENCE: 11

Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
            20                  25                  30

Arg Val Gln Gln Asn Val Pro Ser Gly Thr Asp Thr Gly Asp Pro Gln
        35                  40                  45

Ser Lys Pro Leu Gly Asp Trp Ala Ala Gly Thr Met Asp Pro Glu Ser
    50                  55                  60

Ser Ile Phe Ile Glu Asp Ala Ile Lys Tyr Phe Lys Glu Lys Val Ser
65                  70                  75                  80

Ile Gln Asn Leu Leu Leu Leu Thr Asp Asn Glu Ala Trp Asn Gly
                85                  90                  95

Phe Val Ala Ala Ala Glu Leu Pro Arg Asn Glu Ala Asp Glu Leu Arg
            100                 105                 110

Lys Ala Leu Asp Asn Leu Ala Arg Gln Met Ile Met Lys Asp Lys Asn
        115                 120                 125

Trp His Asp Lys Gly Gln Gln Tyr Arg Asn Trp Phe Leu Lys Glu Phe
    130                 135                 140

Pro Arg Leu Lys Ser Lys Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
    210                 215                 220

Ser Ser Thr Ile Asp Tyr Gly Lys Lys Trp Trp Thr Gln Ala Gln Ala
225                 230                 235                 240

His Asp Leu Val Ile Lys Ser Leu Asp Lys Leu Lys Glu Val Lys Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
        275                 280                 285

Ala Arg Ala Asn Leu Gln Ser Val Pro His Ala Ser Ala Ser Arg Pro
    290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu

```
             340                 345                 350
Val Tyr Glu Ser Lys His Leu His Glu Gly Ala Lys Ser Glu Thr Ala
            355                 360                 365

Glu Glu Leu Lys Lys Val Ala Gln Glu Leu Glu Lys Leu Asn Ile
        370                 375                 380

Leu Asn Asn Asn Tyr Lys Ile Leu Gln Ala Asp Gln Glu Leu Leu Glu
385                 390                 395                 400

Ser Arg Gly Pro Phe Glu Gly Lys Pro Ile Pro Asn Pro Leu Leu Gly
                405                 410                 415

Leu Asp Ser Thr Arg Thr Gly His His His His Gly Ser Gly
            420                 425                 430

Ala Thr Asn Phe Ser Leu Leu Lys Gln Ala Gly Asp Val Glu Glu Asn
            435                 440                 445

Pro

<210> SEQ ID NO 12
<211> LENGTH: 73
<212> TYPE: PRT
<213> ORGANISM: Unknown
<220> FEATURE:
<223> OTHER INFORMATION: artificial constructs of Human, viral and
      E-coli Origin

<400> SEQUENCE: 12

Pro Met Lys Gln Arg Ile Thr Val Thr Val Asp Ser Asp Ser Tyr Gln
1               5                   10                  15

Leu Leu Lys Ala Tyr Asp Val Asn Ile Ser Gly Leu Val Ser Thr Thr
            20                  25                  30

Met Gln Asn Glu Ala Arg Arg Leu Arg Ala Glu Arg Trp Lys Ala Glu
        35                  40                  45

Asn Gln Glu Gly Met Ala Glu Val Ala Arg Phe Ile Glu Met Asn Gly
    50                  55                  60

Ser Phe Ala Asp Glu Asn Arg Asp Trp
65                  70

<210> SEQ ID NO 13
<211> LENGTH: 7238
<212> TYPE: DNA
<213> ORGANISM: Unknown
<220> FEATURE:
<223> OTHER INFORMATION: plasmids obtained from E. coli

<400> SEQUENCE: 13
gacgaaaggg cctcgtgata cgcctatttt tataggttaa tgtcatgata ataatggttt      60
cttagtatga tccaatatca aaggaaatga tagcattgaa ggatgagact aatccaattg     120
aggagtggca gcatatagaa cagctaaagg gtagtgctga aggaagcata cgatacccccg    180 catggaatgg gataatatca caggaggtac tagactacct ttcatcctac ataaatagac     240
gcatataagt acgcatttaa gcataaacac gcactatgcc gttcttctca tgtatatata     300
tatacaggca acacgcagat ataggtgcga cgtgaacagt gagctgtatg tgcgcagctc     360
gcgttgcatt tcggaagcg ctcgttttcg gaaacgcttt gaagttccta ttccgaagtt     420
cctattctct agaaagtata ggaacttcag agcgcttttg aaaaccaaaa gcgctctgaa     480
gacgcacttt caaaaaacca aaaacgcacc ggactgtaac gagctactaa aatattgcga     540
ataccgcttc cacaaacatt gctcaaaagt atctctttgc tatatatctc tgtgctatat     600
ccctatataa cctacccatc cacctttcgc tccttgaact tgcatctaaa ctcgacctct     660
```

```
acattttta  tgtttatctc  tagtattact  ctttagacaa  aaaaattgta  gtaagaacta    720
ttcatagagt  gaatcgaaaa  caatacgaaa  atgtaaacat  ttcctatacg  tagtatatag    780
agacaaaata  gaagaaaccg  ttcataattt  tctgaccaat  gaagaatcat  caacgctatc    840
actttctgtt  cacaaagtat  gcgcaatcca  catcggtata  gaatataatc  ggggatgcct    900
ttatcttgaa  aaaatgcacc  cgcagcttcg  ctagtaatca  gtaaacgcgg  gaagtggagt    960
caggcttttt  ttatggaaga  gaaaatagac  accaaagtag  ccttcttcta  accttaacgg   1020
acctacagtg  caaaaagtta  tcaagagact  gcattataga  gcgcacaaag  gagaaaaaaa   1080
gtaatctaag  atgctttgtt  agaaaaatag  cgctctcggg  atgcattttt  gtagaacaaa   1140
aaagaagtat  agattctttg  ttggtaaaat  agcgctctcg  cgttgcattt  ctgttctgta   1200
aaaatgcagc  tcagattctt  tgtttgaaaa  attagcgctc  tcgcgttgca  ttttttgtttt   1260 acaaaaatga  agcacagatt  cttcgttggt  aaaatagcgc  tttcgcgttg  catttctgtt   1320
ctgtaaaaat  gcagctcaga  ttctttgttt  gaaaaattag  cgctctcgcg  ttgcatttt   1380 gttctacaaa  atgaagcaca  gatgcttcgt  tcaggtggca  cttttcgggg  aaatgtgcgc   1440 ggaacccta  tttgtttatt  tttctaaata  cattcaaata  tgtatccgct  catgagacaa   1500
taaccctgat  aaatgcttca  ataatattga  aaaggaaga  gtatgagtat  tcaacatttc   1560
cgtgtcgccc  ttattccctt  ttttgcggca  ttttgccttc  ctgttttgc  tcacccagaa   1620 acgctggtga  agtaaaaga  tgctgaagat  cagttgggtg  cacgagtggg  ttacatcgaa   1680
ctggatctca  acagcggtaa  gatccttgag  agttttcgcc  ccgaagaacg  ttttccaatg   1740
atgagcactt  ttaaagttct  gctatgtggc  gcggtattat  cccgtattga  cgccgggcaa   1800
gagcaactcg  gtcgccgcat  acactattct  cagaatgact  tggttgagta  ctcaccagtc   1860
acagaaaagc  atcttacgga  tggcatgaca  gtaagagaat  tatgcagtgc  tgccataacc   1920
atgagtgata  acactgcggc  caacttactt  ctgacaacga  tcggaggacc  gaaggagcta   1980
accgcttttt  tgcacaacat  gggggatcat  gtaactcgcc  ttgatcgttg  ggaaccggag   2040
ctgaatgaag  ccataccaaa  cgacgagcgt  gacaccacga  tgcctgtagc  aatggcaaca   2100
acgttgcgca  aactattaac  tggcgaacta  cttactctag  cttcccggca  acaattaata   2160
gactggatgg  aggcggataa  agttgcagga  ccacttctgc  gctcggccct  tccggctggc   2220
tggtttattg  ctgataaatc  tggagccggt  gagcgtgggt  ctcgcggtat  cattgcagca   2280
ctggggccag  atggtaagcc  ctcccgtatc  gtagttatct  acacgacggg  gagtcaggca   2340
actatggatg  aacgaaatag  acagatcgct  gagataggtg  cctcactgat  taagcattgg   2400
taactgtcag  accaagttta  ctcatatata  ctttagattg  atttaaaact  tcatttttaa   2460
tttaaaagga  tctaggtgaa  gatcctttt  gataatctca  tgaccaaaat  cccttaacgt   2520
gagttttcgt  tccactgagc  gtcagacccc  gtagaaaaga  tcaaaggatc  ttcttgagat   2580 ccttttttc  tgcgcgtaat  ctgctgcttg  caaacaaaaa  aaccaccgct  accagcggtg   2640
gtttgtttgc  cggatcaaga  gctaccaact  cttttccga  aggtaactgg  cttcagcaga   2700
gcgcagatac  caaatactgt  ccttctagtg  tagccgtagt  taggccacca  cttcaagaac   2760
tctgtagcac  cgcctacata  cctcgctctg  ctaatcctgt  taccagtggc  tgctgccagt   2820
ggcgataagt  cgtgtcttac  cgggttggac  tcaagacgat  agttaccgga  taaggcgcag   2880
cggtcgggct  gaacggggg  ttcgtgcaca  cagcccagct  tggagcgaac  gacctacacc   2940
gaactgagat  acctacagcg  tgagctatga  gaaagcgcca  cgcttcccga  agggagaaag   3000
```

```
gcggacaggt atccggtaag cggcagggtc ggaacaggag agcgcacgag ggagcttcca    3060
gggggaaacg cctggtatct ttatagtcct gtcgggtttc gccacctctg acttgagcgt    3120
cgattttttgt gatgctcgtc aggggggcgg agcctatgga aaaacgccag caacgcggcc   3180
ttttttacggt tcctggcctt tgctggcct tttgctcaca tgttctttcc tgcgttatcc    3240
cctgattctg tggataaccg tattaccgcc tttgagtgag ctgataccgc tcgccgcagc    3300
cgaacgaccg agcgcagcga gtcagtgagc gaggaagcgg aagagcgccc aatacgcaaa    3360
ccgcctctcc ccgcgcgttg gccgattcat taatgcagct ggcacgacag gtttcccgac    3420
tggaaagcgg gcagtgagcg caacgcaatt aatgtgagtt acctcactca ttaggcaccc    3480
caggctttac actttatgct tccggctcct atgttgtgtg gaattgtgag cggataacaa    3540
tttcacacag gaaacagcta tgaccatgat tacgccaagc gcgcaattaa ccctcactaa    3600
agggaacaaa agctggagct ccggatgcaa gggttcgaat cccttagctc tcattatttt    3660
ttgcttttc tcttgaggtc acatgatcgc aaaatggcaa atggcacgtg aagctgtcga    3720
tattggggaa ctgtggtggt tggcaaatga ctaattaagt tagtcaaggc gccatcctca    3780
tgaaaactgt gtaacataat aaccgaagtg tcgaaaaggt ggcaccttgt ccaattgaac    3840
acgctcgatg aaaaaaataa gatatatata aggttaagta aagcgtctgt tagaaaggaa    3900
gttttttcctt tttcttgctc tcttgtcttt tcatctacta tttccttcgt gtaatacagg    3960
gtcgtcagat acatagatac aattctatta cccccatcca tactctagaa ctagtggatc    4020
ccccgggctg caggaattcg atatcaagct tatcgatacc gtcgacctcg agtcatgtaa    4080
ttagttatgt cacgcttaca ttcacgcccc cccccacat ccgctctaac cgaaaaggaa    4140
ggagttagac aacctgaagt ctaggtccct atttattttt ttatagttat gttagtatta    4200
agaacgttat ttatatttca aattttttctt tttttctgt acagacgcgt gtacgcatgt    4260
aacattatac tgaaaaccctt gcttgagaag ttttgggac gctcgaaggc tttaatttgc    4320
ggccggtacc caattcgccc tatagtgagt cgtattacgc gcgctcactg gccgtcgttt    4380
tacaacgtcg tgactgggaa accctggcg ttacccaact taatcgcctt gcagcacatc    4440
cccctttcgc cagctggcgt aatagcgaag aggcccgcac cgatcgccct tcccaacagt    4500
tgcgcagcct gaatggcgaa tggcgcgacg cgccctgtag cggcgcatta agcgcggcgg    4560
gtgtggtggt tacgcgcagc gtgaccgcta cacttgccag cgccctagcg cccgctcctt    4620
tcgctttctt cccttccttt ctcgccacgt tcgccggctt tccccgtcaa gctctaaatc    4680
gggggctccc tttagggttc cgatttagtg ctttacggca cctcgacccc aaaaaacttg    4740
attagggtga tggttcacgt agtgggccat cgccctgata cggttttt cgccctttga    4800
cgttggagtc cacgttcttt aatagtggac tcttgttcca aactggaaca cactcaacc    4860
ctatctcggt ctattctttt gatttataag ggattttgcc gatttcggcc tattggttaa    4920
aaaatgagct gatttaacaa aaatttaacg cgaattttaa caaaatatta acgtttacaa    4980
tttcctgatg cggtattttc tccttacgca tctgtgcggt atttcacacc gcatagggta    5040
ataactgata taattaaatt gaagctctaa tttgtgagtt tagtatacat gcatttactt    5100
ataatacagt tttgtgggaa tactcaggta tcgtaagatg caagagttcg aatctcttag    5160
caaccattat tttttttcctc aacataacga gaacacacag gggcgctatc gcacagaatc    5220
aaattcgatg actggaaatt ttttgttaat ttcagaggtc gcctgacgca tatacctttt    5280
tcaactgaaa aattgggaga aaaaggaaag gtgagagccg cggaaccggc ttttcatata    5340
gaatagagaa gcgttcatga ctaaatgctt gcatcacaat acttgaagtt gacaatatta    5400
```

```
tttaaggacc tattgttttt tccaataggt ggttagcaat cgtcttactt tctaactttt    5460 cttaccttt  acatttcagc aatatatata tatatatttc aaggatatac cattctaatg    5520 tctgcccta  agaagatcgt cgttttgcca ggtgaccacg ttggtcaaga aatcacagcc    5580
gaagccatta aggttcttaa agctatttct gatgttcgtt ccaatgtcaa gttcgatttc    5640
gaaaatcatt taattggtgg tgctgctatc gatgctacag gtgttccact tccagatgag    5700
gcgctggaag cctccaagaa ggctgatgcc gttttgttag gtgctgtggg tggtcctaaa    5760
tggggtaccg gtagtgttag acctgaacaa ggtttactaa aaatccgtaa agaacttcaa    5820
ttgtacgcca acttaagacc atgtaacttt gcatccgact ctcttttaga cttatctcca    5880
atcaagccac aatttgctaa aggtactgac ttcgttgttg tcagagaatt agtgggaggt    5940
atttactttg gtaagagaaa ggaagacgat ggtgatggtg tcgcttggga tagtgaacaa    6000
tacaccgttc cagaagtgca aagaatcaca agaatggccg ctttcatggc cctacaacat    6060
gagccaccat tgcctatttg gtccttggat aaagctaatg ttttggcctc ttcaagatta    6120
tggagaaaaa ctgtggagga aaccatcaag aacgaattcc ctacattgaa ggttcaacat    6180
caattgattg attctgccgc catgatccta gttaagaacc caacccacct aaatggtatt    6240
ataatcacca gcaacatgtt tggtgatatc atctccgatg aagcctccgt tatcccaggt    6300
tccttgggtt tgttgccatc tgcgtccttg gcctctttgc cagacaagaa caccgcattt    6360
ggtttgtacg aaccatgcca cggttctgct ccagatttgc caaagaataa ggtcaaccct    6420
atcgccacta tcttgtctgc tgcaatgatg ttgaaattgt cattgaactt gcctgaagaa    6480
ggtaaggcca ttgaagatgc agttaaaaag gttttggatg caggtatcag aactggtgat    6540
ttaggtggtt ccaacagtac caccgaagtc ggtgatgctg tcgccgaaga agttaagaaa    6600
atccttgctt aaaaagattc tctttttta tgatatttgt acataaactt tataaatgaa    6660
attcataata gaaacgacac gaaattacaa aatggaatat gttcatagg  tagacgaaac    6720 tatatacgca atctacatac atttatcaag aaggagaaaa aggaggatgt aaaggaatac    6780
aggtaagcaa attgatacta atggctcaac gtgataagga aagatttatc ttcgtttcct    6840
gcaggttttt gttctgtgca gttgggttaa gaatactggg caatttcatg tttcttcaac    6900
actacatatg cgtatatata ccaatctaag tctgtgctcc ttccttcgtt cttccttctg    6960
ttcggagatt accgaatcaa aaaatttca aagaaaccga aatcaaaaaa aagaataaaa    7020
aaaaaatgat gaattgaatt gaaaagctgt ggtatggtgc actctcagta caatctgctc    7080
tgatgccgca tagttaagcc agccccgaca cccgccaaca cccgctgacg cgccctgacg    7140
ggcttgtctg ctcccggcat ccgcttacag acaagctgtg accgtctccg ggagctgcat    7200
gtgtcagagg ttttcaccgt catcaccgaa acgcgcga                             7238

<210> SEQ ID NO 14
<211> LENGTH: 5575
<212> TYPE: DNA
<213> ORGANISM: Unknown
<220> FEATURE:
<223> OTHER INFORMATION: plasmids obtained from E. coli

<400> SEQUENCE: 14
gacgaaaggg cctcgtgata cgcctatttt tataggttaa tgtcatgata ataatggttt      60
cttaggacgg atcgcttgcc tgtaacttac acgcgcctcg tatcttttaa tgatggaata    120
atttgggaat ttactctgtg tttatttatt tttatgtttt gtatttggat tttagaaagt    180
```

-continued

```
aaataaagaa ggtagaagag ttacggaatg aagaaaaaaa aataaacaaa ggtttaaaaa      240
atttcaacaa aaagcgtact ttacatatat atttattaga caagaaaagc agattaaata      300
gatatacatt cgattaacga taagtaaaat gtaaaatcac aggattttcg tgtgtggtct      360
tctacacaga caagatgaaa caattcggca ttaatacctg agagcaggaa gagcaagata      420
aaaggtagta tttgttggcg atcccctag agtctttac atcttcggaa aacaaaaact       480 atttttctt taatttcttt ttttacttc tattttaat ttatatattt atattaaaaa       540
atttaaatta taattatttt tatagcacgt gatgaaaagg acccaggtgg cacttttcgg      600
ggaaatgtgc gcggaacccc tatttgttta tttttctaaa tacattcaaa tatgtatccg      660
ctcatgagac aataaccctg ataaatgctt caataatatt gaaaaggaa gagtatgagt      720 attcaacatt tccgtgtcgc ccttattccc tttttgcgg cattttgcct tcctgttttt       780
gctcacccag aaacgctggt gaaagtaaaa gatgctgaag atcagttggg tgcacgagtg      840
ggttacatcg aactggatct caacagcggt aagatccttg agagttttcg ccccgaagaa      900
cgttttccaa tgatgagcac ttttaaagtt ctgctatgtg gcgcggtatt atcccgtatt      960
gacgccgggc aagagcaact cggtcgccgc atacactatt ctcagaatga cttggttgag     1020
tactcaccag tcacagaaaa gcatcttacg gatggcatga cagtaagaga attatgcagt     1080
gctgccataa ccatgagtga taacactgcg gccaacttac ttctgacaac gatcggagga     1140
ccgaaggagc taaccgcttt tttgcacaac atggggatc atgtaactcg ccttgatcgt      1200
tgggaaccgg agctgaatga agccatacca aacgacgagc gtgacaccac gatgcctgta     1260
gcaatggcaa caacgttgcg caaactatta actggcgaac tacttactct agcttccgg      1320 caacaattaa tagactggat ggaggcggat aaagttgcag gaccacttct gcgctcggcc     1380
cttccggctg gctggtttat tgctgataaa tctggagccg gtgagcgtgg gtctcgcggt     1440
atcattgcag cactggggcc agatggtaag ccctcccgta tcgtagttat ctacacgacg     1500
gggagtcagg caactatgga tgaacgaaat agacagatcg ctgagatagg tgcctcactg     1560
attaagcatt ggtaactgtc agaccaagtt tactcatata tactttagat tgatttaaaa     1620 cttcatttt aatttaaaag gatctaggtg aagatccttt tgataatct catgaccaaa       1680 atcccttaac gtgagttttc gttccactga gcgtcagacc ccgtagaaaa gatcaaagga     1740
tcttcttgag atcctttttt tctgcgcgta atctgctgct tgcaaacaaa aaaaccaccg     1800
ctaccagcgg tggtttgttt gccggatcaa gagctaccaa ctcttttcc gaaggtaact      1860 ggcttcagca gagcgcagat accaaatact gtccttctag tgtagccgta gttaggccac     1920
cacttcaaga actctgtagc accgcctaca tacctcgctc tgctaatcct gttaccagtg     1980
gctgctgcca gtggcgataa gtcgtgtctt accgggttgg actcaagacg atagttaccg     2040
gataaggcgc agcggtcggg ctgaacgggg ggttcgtgca cacagcccag cttggagcga     2100
acgacctaca ccgaactgag atacctacag cgtgagctat gagaaagcgc cacgcttccc     2160
gaagggagaa aggcggacag gtatccggta agcggcaggg tcggaacagg agagcgcacg     2220
agggagcttc caggggaaa cgcctggtat ctttatagtc ctgtcgggtt tcgccacctc      2280
tgacttgagc gtcgattttt gtgatgctcg tcagggggc ggagcctatg gaaaacgcc       2340 agcaacgcgg cctttttacg gttcctggcc ttttgctggc cttttgctca catgttcttt     2400
cctgcgttat cccctgattc tgtggataac cgtattaccg cctttgagtg agctgatacc     2460
gctcgccgca gccgaacgac cgagcgcagc gagtcagtga gcgaggaagc ggaagagcgc     2520
ccaatacgca aaccgcctct ccccgcgcgt tggccgattc attaatgcag ctggcacgac     2580
```

```
aggtttcccg actggaaagc gggcagtgag cgcaacgcaa ttaatgtgag ttacctcact      2640
cattaggcac cccaggcttt acactttatg cttccggctc ctatgttgtg tggaattgtg      2700
agcggataac aatttcacac aggaaacagc tatgaccatg attacgccaa gcgcgcaatt      2760
aaccctcact aaagggaaca aaagctggag ctcttgaagt acggattaga agccgccgag      2820
cgggcgacag ccctccgacg gaagactctc ctccgtgcgt cctcgtcttc accggtcgcg      2880
ttcctgaaac gcagatgtgc ctcgcgccgc actgctccga acaataaaga ttctacaata      2940
ctagctttta tggttatgaa gaggaaaaat tggcagtaac ctggccccac aaaccttcaa      3000
attaacgaat caaattaaca accataggat gataatgcga ttagtttttt agccttattt      3060
ctggggtaat taatcagcga agcgatgatt tttgatctat taacagatat ataaatggaa      3120
aagctgcata accactttaa ctaatacttt caacattttc agtttgtatt acttcttatt      3180
caaatgtcat aaaagtatca acaaaaaatt gttaatatac ctctatactt taacgtcaag      3240
gagaaaaaac tatatctaga actagtggat ccccccgggct gcaggaattc gatatcaagc      3300
ttatcgatac cgtcgacctc gagacaggcc cttttccctt tgtcgatatc atgtaattag      3360
ttatgtcacg cttacattca cgccctcctc ccacatccgc tctaaccgaa aaggaaggag      3420
ttagacaacc tgaagtctag gtccctattt attttttta atagttatgt tagtattaag      3480
aacgttattt atatttcaaa ttttttcttt tttctgtac aaacgcgtgt acgcatgtaa      3540
cattatactg aaaaccttgc ttgagaggta cccaattcgc cctatagtga gtcgtattac      3600
gcgcgctcac tggccgtcgt tttacaacgt cgtgactggg aaaaccctgg cgttacccaa      3660
cttaatcgcc ttgcagcaca tcccccttc gccagctggc gtaatagcga agaggcccgc      3720
accgatcgcc cttcccaaca gttgcgcagc ctgaatggcg aatggcgcga cgcgccctgt      3780
agcggcgcat taagcgcggc gggtgtggtg gttacgcgca gcgtgaccgc tacacttgcc      3840
agcgccctag cgcccgctcc tttcgctttc ttcccttcct ttctcgccac gttcgccggc      3900
tttccccgtc aagctctaaa tcggggggctc cctttagggt tccgatttag tgctttacgg      3960
cacctcgacc ccaaaaaact tgattagggt gatggttcac gtagtgggcc atcgccctga      4020
tagacggttt ttcgcccttt gacgttggag tccacgttct ttaatagtgg actcttgttc      4080
caaactggaa caacactcaa ccctatctcg gtctattctt ttgatttata agggattttg      4140
ccgatttcgg cctattggtt aaaaatgag ctgatttaac aaaaatttaa cgcgaatttt      4200
aacaaaatat taacgtttac aatttcctga tgcggtattt tctccttacg catctgtgcg      4260
gtatttcaca ccgcataggg taataactga tataattaaa ttgaagctct aatttgtgag      4320
tttagtatac atgcatttac ttataataca gttttttagt tttgctggcc gcatcttctc      4380
aaatatgctt cccagcctgc ttttctgtaa cgttcaccct ctaccttagc atcccttccc      4440
tttgcaaata gtcctcttcc aacaataata atgtcagatc ctgtagagac cacatcatcc      4500
acggttctat actgttgacc caatgcgtct cccttgtcat ctaaaccac accgggtgtc      4560 ataatcaacc aatcgtaacc ttcatctctt ccacccatgt ctctttgagc aataaagccg      4620
ataacaaaat ctttgtcgct cttcgcaatg tcaacagtac ccttagtata ttctccagta      4680
gatagggagc ccttgcatga caattctgct aacatcaaaa ggcctctagg ttcctttgtt      4740
acttcttctg ccgcctgctt caaaccgcta acaatacctg ggcccaccac accgtgtgca      4800
ttcgtaatgt ctgcccattc tgctattctg tatacacccg cagagtactg caatttgact      4860
gtattaccaa tgtcagcaaa ttttctgtct tcgaagagta aaaaattgta cttggcggat      4920
```

| | |
|---|---|
| aatgccttta gcggcttaac tgtgccctcc atggaaaaat cagtcaagat atccacatgt | 4980 |
| gtttttagta aacaaatttt gggacctaat gcttcaacta actccagtaa ttccttggtg | 5040 |
| gtacgaacat ccaatgaagc acacaagttt gtttgctttt cgtgcatgat attaaatagc | 5100 |
| ttggcagcaa caggactagg atgagtagca gcacgttcct tatatgtagc tttcgacatg | 5160 |
| atttatcttc gtttcctgca ggttttttgtt ctgtgcagtt gggttaagaa tactgggcaa | 5220 |
| tttcatgttt cttcaacact acatatgcgt atatatacca atctaagtct gtgctccttc | 5280 |
| cttcgttctt ccttctgttc ggagattacc gaatcaaaaa aatttcaaag aaaccgaaat | 5340 |
| caaaaaaaag aataaaaaaa aaatgatgaa ttgaattgaa aagctgtggt atggtgcact | 5400 |
| ctcagtacaa tctgctctga tgccgcatag ttaagccagc cccgacaccc gccaacaccc | 5460 |
| gctgacgcgc cctgacgggc ttgtctgctc ccggcatccg cttacagaca agctgtgacc | 5520 |
| gtctccggga gctgcatgtg tcagaggttt tcaccgtcat caccgaaacg cgcga | 5575 |

<210> SEQ ID NO 15
<211> LENGTH: 1038
<212> TYPE: DNA
<213> ORGANISM: Unknown
<220> FEATURE:
<223> OTHER INFORMATION: artificial constructs of Human, viral and
      E-coli Origin

<400> SEQUENCE: 15

| | |
|---|---|
| atgagtaaag gagaagaact tttcactgga gttgtcccaa ttcttgttga attagatggt | 60 |
| gatgttaatg ggcacaaatt ttctgtcagt ggagagggtg aaggtgatgc aacatacgga | 120 |
| aaacttaccc ttaaatttat ttgcactact ggaaaactac ctgttccatg gccaacactt | 180 |
| gtcactactt tcgcgtatgg tcttcaatgc tttgcgagat acccagatca tatgaaacag | 240 |
| catgactttt tcaagagtgc catgcccgaa ggttatgtac aggaaagaac tatattttc | 300 |
| aaagatgacg ggaactacaa gacacgtgct gaagtcaagt ttgaaggtga taccctttgtt | 360 |
| aatagaatcg agttaaaagg tattgatttt aagaagatg gaaacattct tggacacaaa | 420 |
| ttggaataca actataactc acacaatgta tacatcatgg cagacaaaca aaagaatgga | 480 |
| atcaaagtta acttcaaaat tagacacaac attgaagatg aagcgttca actagcagac | 540 |
| cattatcaac aaaatactcc aattggcgat ggccctgtcc ttttaccaga caaccattac | 600 |
| ctgtccacac aatctgccct ttcgaaagat cccaacgaaa agagagacca catggtcctt | 660 |
| cttgagtttg taacagctgc tgggattacc catggtatgg atgaattgta caaggaagc | 720 |
| ggagctacta acttcagcct gctgaagcag gctggagacg tggaggagaa ccctggacct | 780 |
| cacactacta gattgaagag agttggtggt tctgttatgt tgactgttcc accagctttg | 840 |
| ttgaacgctt tgtctttggg tactgacaac gaagttggta tggttattga caacggtaga | 900 |
| ttgattgttg aaccatacag aagaccacaa tactctttgg ctgaattgtt ggctcaatgt | 960 |
| gacccaaacg ctgaaatttc tgctgaagaa agagaatggt tggacgctcc agctactggt | 1020 |
| caagaagaaa tttaataa | 1038 |

<210> SEQ ID NO 16
<211> LENGTH: 405
<212> TYPE: DNA
<213> ORGANISM: Unknown
<220> FEATURE:
<223> OTHER INFORMATION: poison kid sequence isolated from E. coli

<400> SEQUENCE: 16

-continued

```
atgttgaagt accaattgaa gaacgaaaac ggttggatgc acagaagatt ggttagaaga      60
aagtctgaca tggaaagagg tgaaatttgg ttggtttctt tggacccaac tgctggtcac     120
gaacaacaag gtactagacc agttttgatt gttactccag ctgctttcaa cagagttact     180
agattgccag ttgttgttcc agttacttct ggtggtaact tcgctagaac tgctggtttc     240
gctgtttctt tggacggtgt tggtattaga actactggtg ttgttagatg tgaccaacca     300
agaactattg acatgaaggc tagaggtggt aagagattgg aaagagttcc agaaactatt     360
atgaacgaag ttttgggtag attgtctact attttgactt aataa                    405
```

METHOD AND SYSTEM FOR THE PRODUCTION OF RECOMBINANT PROTEINS BY CELLS

This application is a National Stage Application of International Patent Application No. PCT/EP2015/065350, filed 6 Jul. 2015, which claims benefit of Serial No. PCT/EP2014/064355, filed 4 Jul. 2014 in Europe and which applications are incorporated herein by reference. To the extent appropriate, a claim of priority is made to each of the above disclosed applications.

FIELD OF THE INVENTION

The present invention is in the field of biotechnology and is related to a method and means allowing through molecular cloning of cells, an improved production of recombinant peptides or proteins by cells, possibly present in a bioreactor.

BACKGROUND OF THE INVENTION AND STATE OF THE ART

Typically, production process of peptide or protein of interest by host cells, or molecular cloning, requires the use of one or more replicon sequence(s), such as plasmids carrying one or more gene(s) encoding the protein(s) of interest.

Cells in bioreactor present usually a high heterogeneity. It has been demonstrated that the growth of plasmid bearing cells, especially bacterial cells, is significantly reduced compared to plasmid free host cells. Indeed, peptide or protein production coming from gene of interest overproduction represents a significant burden on the metabolism of the cell.

Therefore, it is necessary to select cells that keep in their (chromosomal or extrachromosomal) genome the gene of interest.

This selection is efficiently done by the use of a selectable marker, such as antibiotic resistance gene or pair of poison and/or antidote genes.

Poison (or toxin) and antidote (or antitoxin) genes are sequences naturally found in plasmids, chromosomes and bacteriophages.

A poison gene, or a nucleotide sequence of such a gene, will code for a stable peptide or protein whereas its corresponding antidote gene can code for another peptide, protein or an RNA, stable or unstable, that may neutralize the poison peptide or protein either transcriptionally or post-transcriptionally or post-translationally or via protein-protein or RNA-protein interaction(s).

Because it represents a burden to cell metabolism, bacteria will not always produce the recombinant peptide or proteins efficiently. Indeed, it is possible that non desired genetic modifications are generated in the protein coding sequence, for instance point mutations (nucleotide(s) substitutions), deletions or additions of one or more nucleotide(s) in the recombinant nucleotide(s) sequence(s) of interest will occur and will generate stop codons, frameshifts and/or deletion or insertion in the corresponding amino acid sequence(s) and maintain the production of inactive, mutated or truncated peptides or proteins. At the level of transcription, errors can also occur such as nucleotide(s) substitution(s), deletions or additions of one or more nucleotide(s), or premature arrest of transcription, resulting in aberrant messenger RNA, which produce inactive, mutated or truncated peptides or proteins. Even in the absence of errors at the genetic or messenger RNA levels, errors can occur during translation such as frameshifts or premature arrest of translation, which also produce inactive, mutated or truncated peptides or proteins. In addition, mutations can occur elsewhere in the genome (including chromosomal and extra-chromosomal elements), which can directly or indirectly affect the yield and quality of the recombinant protein or peptide, such as mutations affecting the promoter or operator region of the gene encoding the protein or peptide, or mutations affecting the expression of components of the transcriptional or translational machineries.

In addition, due to high heterogeneity in bioreactors, some cells show no or low recombinant peptide or protein production.

Therefore, it still exists a need to improve methods and systems to guarantee better quality of recombinant peptides or proteins, particularly of full-length recombinant peptides or proteins showing the expected primary amino acid sequence, and to guarantee homogeneous producing-cell population, possibly present in a bioreactor.

Aims of the Invention

The present invention aims to provide a method and means for the transformation of cells, a method for controlling the viability of these transformed cells, or means, that do not present the drawbacks of the state of the art.

The aim of the present invention is to provide a method and means of improving the production of recombinant peptides or proteins bearing the expected, full length primary amino acid sequences of interest. Preferably, the present invention aims to provide a simple and improved method for the transformation of cells, in particular through the use a new nucleic acid construct possibly present into an adequate vector or as a chromosomally integrated sequence in the cell and that comprises genetic elements for performing such method(s) to push these cells for an efficient production of these peptides or proteins of interest at a high production yield with a high quality yield.

A preferred aim of the present invention is to provide a method and means of improving the quality and homogeneity of recombinant peptides or proteins of interest produced by cells possibly present in a bioreactor, especially recombinant peptides or proteins affected by genetically encoded modifications (nucleotide(s) substitution(s), addition(s) or deletion(s)) in their coding sequence or at any other location in the host cell genome, modifications originating from transcriptional errors (nucleotide(s) substitution(s), addition(s) or deletion(s), premature arrest of transcription), or modifications occurring at the translational level (ribosome frameshifting, premature arrest of translation).

SUMMARY OF THE INVENTION

The present invention is related to a cassette sequence, i.e. a nucleic acid sequence, possibly present in a vector for the transformation of a host cell, said cassette sequence comprising at least:
- one or more copies of a first nucleotide sequence encoding a peptide or a protein of interest to be produced by this host cell and being linked to
- one or more copies of a second nucleotide sequence either providing a resistance to a toxin, that is toxic for the host cell, or encoding an antitoxin peptide or protein or RNA to a toxin peptide or protein, wherein these first and second nucleotide sequences are organized in such a way that production of the peptide encoded by the second nucleotide sequence(s) is translationally coupled to production of the peptide encoded by the first nucleotide sequence. Translational coupling refers to any physiological mechanism by which production of the peptide encoded by the second nucleotide sequence(s) can only occur when the peptide encoded by the first nucleotide sequence has been correctly completed by the translation machinery of the host cell. Translational coupling includes but is not limited to production of fusion proteins.

Preferably, the cassette sequence according to the invention further comprises, disposed between the first and the second nucleotide sequences, a third nucleotide sequence encoding a linker peptide of at least 2 amino acids, preferably of (about) 2 to (about) 500 amino acids and wherein these first, second and third nucleotide sequences are organized in such a way that production of the peptide encoded by the second nucleotide sequence(s) is translationally coupled to production of the peptide encoded by the first nucleotide sequence.

According to the invention, the linker peptide encoded by the third sequence of the cassette sequence, preferably presents one of the following characteristics:

the linker peptide comprises a sequence cleavable by a protease, preferably a Tobacco Etch Virus (TEV) protease (Miladi, B. et al. 2012. J. Biotechnol. 128, 97-103);

the linker peptide is an auto-cleavable peptide, preferably an intein (Cui et al. (2006) Prot. Expr. Purif. 50:74);

the linker peptide induces ribosome skipping or STOPGO or STOP CARRY-ON leading to the production of two peptides, preferably a member of the peptides 2A family (Sharma, P. et al., 2012. Nucl. Acids Res., 40(7), pp. 3143-3151).

Preferably, the toxin is an antibiotic or a mixture of antibiotics and the second nucleotide sequence encodes a peptide providing for the host cell resistance to an antibiotic or a mixture of antibiotics or is a mutated target sequence of the antibiotic or mixture of antibiotics, or the toxin is an herbicide or fungicide and the second nucleotide sequence encodes a peptide providing for the host cell resistance to the herbicide or the fungicide or is a mutated target sequence of the herbicide or a mutated target of the fungicide. Preferably, the antibiotic, mixture of antibiotics, herbicide or fungicide is added to the culture medium. The antibiotic, mixture of antibiotics, herbicide or fungicide can also be produced by the host cell itself, by introducing the nucleotide sequence encoding the necessary biosynthetic pathway in the host cell, preferably in the chromosome of the host cell and preferably under the control of a first inducible promoter/operator sequence.

More preferably, the toxin is a peptide or a protein belonging to a toxin/antitoxin module, and the second nucleotide sequence encodes the associated antitoxin peptide or RNA that may neutralize the toxin. Toxin/antitoxins pairs may selected from the group consisting of CcdB/CcdA, Kid/Kis (PemK/PemI), ParE/ParD, MazE/MazF, RelE/RelB, YafO/YafN, HipA/HipB, Doc/PhD, VapC/VapB, VapD/VapX, HicA/HicB, YoeB/YefN, YafQ/DinJ, Tse2/Tsi2 (PA2702/PA2703), Tse1 (PA1844)/Tsi1, Tse3 (PA3484)/Tsi3, C-terminal portions of Rhs (Rhs-CT) or CdiA (Cdi-CT) peptides/associated immune peptides RhsI or CdiI, or bacteriocins peptides being of plasmid origin or not. The toxin can be added to the culture medium. The toxin can also be produced by the host cell itself, by introducing the nucleotide sequence encoding the toxin in the host cell, preferably in the chromosome of the host cell and preferably under the control of a first inducible promoter/operator sequence.

The present invention concerns also the vector, preferably a plasmid, comprising the coding sequences of the cassette according to the invention, preferably under the control of a second promoter/operator sequence. According to another embodiment of the present invention, this cassette sequence can also be integrated, preferably under the control of a second promoter/operator sequence, into the genome of the host cell, preferably into the chromosome of this host cell.

In the present invention, the vector is preferably a plasmid suitable for transformation of a host prokaryotic or eukaryotic cell, animal, plant, including protoplast, fungi including a yeast cell (such a *Pichia* or *Saccharomyces*), more preferably a bacterial cell, such as *E. coli*.

Preferably, both first and second promoter/operator sequences above described, i.e. the first inducible promoter/operator sequence controlling the sequence(s) encoding the toxin and the second promoter/operator sequence controlling the cassette sequence, are different promoter/operator sequences.

Another aspect of the present invention is related to the host cells transformed by the cassette sequence or the vector, or nucleic acid construct, according to the invention, preferably a host cell comprising in its genome, preferably under the control of a first promoter/operator sequence, a nucleotide sequence encoding the toxin that is toxic (preferably lethal) for this cell and further comprising the cassette sequence or the vector (nucleic acid construct) according to the invention.

Preferably, the host cell, and the host cell used in the method(s) according to the invention is a bacterial cell, such as *E. coli*, but could be any other suitable host cell for production of nucleic acid, peptide or protein of interest, including eukaryote cells, such as an animal cells, in particular mammalian cells, such as for example CHO or insect cells, fungi including yeast cells (preferably *Pichia* or *Saccharomyces*) and plant cells including protoplasts or plant tissues.

Another aspect of the present invention is related to a method for the transformation of a host cell and production of a peptide or a protein of interest encoded by a first nucleotide sequence, the method comprises the steps of:

putting into contact the cassette sequence or the vector, or nucleic acid construct, according to the invention with the host cell, preferably the above-described host cell, possibly comprising in its genome, preferably under the control of a promoter/operator sequence, a nucleotide sequence encoding a toxin, which is toxic for this cell, preferably lethal for this cell, and/or wherein this toxin is present in the culture medium and/or the culture medium comprises a cell (which can be the host cell or a cell which is not the host cell) and secreting in the culture medium this toxin; and recovering from the culture medium either the fusion protein or the peptide (or protein) of interest, possibly after a cleavage of the linker peptide.

The present invention is also related to a method for controlling the survivability of a host cell, preferably the above-described cell comprising in its genome the nucleotide sequence of the cassette or the vector according to the invention and wherein:

either the host cell further comprises in its genome, preferably under the control of a first promoter/operator sequence, one or more copies of a fourth nucleotide sequence encoding the toxin or the biosynthetic pathway for production of the toxin and/or this host cell further comprising in its culture medium this toxin or cell (which can be the host cell or a cell which is not the host cell) secreting in this culture medium this toxin.

In the method according to the invention, the nucleotide sequence encoding the toxin or the biosynthetic pathway for the toxin is preferably present in the chromosome of the host cell and the sequence of the vector, or nucleic acid construct, is present upon an extra chromosomal replicon, such as a plasmid.

The present invention concerns also the protein or peptide expression kit, comprising the means for performing the methods according to the invention, preferably the cassette sequence according to the invention, possibly integrated in the vector according to the invention. According to another preferred example, this protein or peptide expression kit, comprises a nucleic acid construct comprising at least one restriction site for (the cloning of) the first nucleotide sequence encoding the peptide (or protein) of interest, this restriction site being disposed upstream the second nucleotide sequence encoding the antitoxin peptide or disposed upstream the third nucleotide sequence encoding the linker peptide and the second nucleotide sequence, theses nucleotides sequences being disposed in such a way that the antitoxin peptide encoded by the second nucleotide sequence is translationally coupled to the peptide of interest (encoded by the first nucleotide sequence), possibly via the linker peptide (encoded by the third nucleotide sequence) as a fusion protein. This means that nucleic acid construct only comprises the second (encoding the antitoxin) nucleotide sequence, or the second (encoding the antitoxin) and third (encoding the linker) nucleotide sequences further including suitable restriction sites for a cloning of the first nucleotide sequence immediately upstream the second or third nucleotide sequence. This nucleic acid construct further comprises before the restriction site(s), the second promoter/activator sequence and all these elements (cassette or nucleic acid construct) are advantageously integrated in the vector according to the invention. In addition, the kit according to the invention may further comprises a sufficient amount of the toxin of the invention to be added to the culture medium and possibly to the host cell above described. The present invention will be further described in the detailed description of the invention and example with the reference to the enclosed figures presented as a non-limiting illustrations of the present invention.

SHORT DESCRIPTION OF THE DRAWINGS

DETAILED DESCRIPTION OF THE INVENTION

Figure 1:
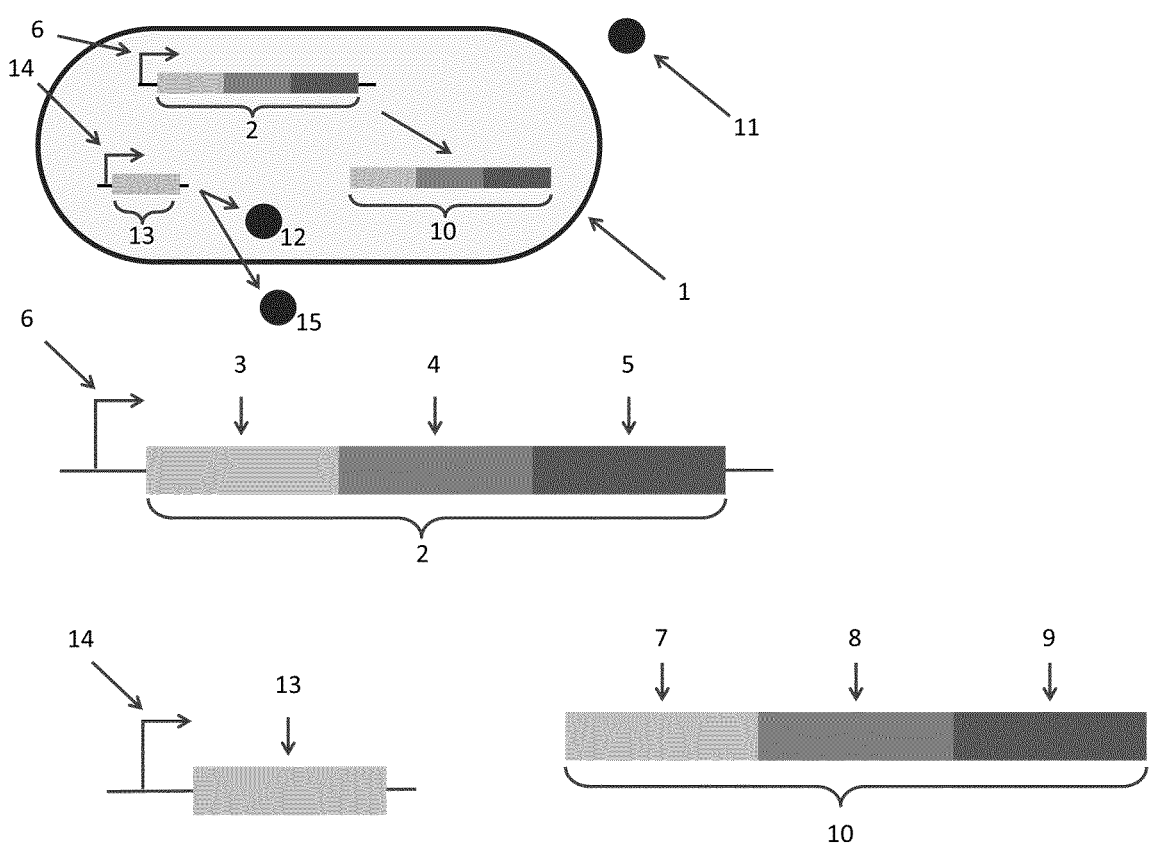
FIG. 1 represents schematically the elements used in the method according to the invention.

As shown in the enclosed FIG. 1, a host cell 1 is transformed by a nucleotide sequence 2, also named hereafter "cassette", possibly incorporated into a transformation or cloning vector or nucleic acid construct.

This vector is preferably a plasmid that may comprise suitable elements for auto-replication into the host cell 1, such as an origin of replication sequence (ori) and an additional promoter/operator sequence(s).

The cassette sequence 2, or the vector incorporating said cassette sequence 2, is used for the transformation of cells, or the cloning of a nucleotide sequence 3 of interest into cells and production of a peptide or a protein of interest 7 by these cells, but also for controlling cells viability. These host cells being preferably selected from the group consisting of bacterial cells or other suitable host cells, such as yeast (preferably *Pichia* or *Saccharomyces*), mammalian, insect cells or plant cells, more preferably *Escherichia coli* (*E. coli*).

Preferably, the vector comprises, the cassette sequence 2 encoding a fusion protein 10 being made of peptides 7,8, and 9, or two separate peptides (peptide 7 with the N-terminal part of linker peptide 8 and C-terminal part of linker peptide 8 with peptide 9) being produced by ribosome skipping, under the control of a first, preferably strong, constitutive, or maybe inducible, promoter and/or operator sequence 6, at least two, preferably three, linked nucleotide sequences, more being preferably made of at least the first nucleotide sequence 3 and the second nucleotide sequence 5, coding for two translationally coupled peptides 7 and 9, as the fusion protein 10.

Figure 2B:
FIG. 2 represents examples of sequences that can be present in the cassette sequence according to the invention.

According to a preferred embodiment of the present invention, the cassette sequence 2 is made of at least:
one or more copies of a first nucleotide sequence 3, or gene of interest encoding a (poly)peptide or protein of interest, such as the APOL-1 peptide or the GFP peptide described in the FIG. 2, this first nucleotide sequence 3 or gene of interest being linked to
one or more copies of a second nucleotide sequence 5 coding for a second peptide 9.

The second nucleotide sequence 5 can either encode an antitoxin peptide or protein, providing resistance to the toxin peptide 11, 12 or 15, produced endogeneously by the host cell 1 (toxin peptide 12) or produced by the host cell 1 and secreted in the culture medium (toxin peptide 15) or added exogenously in the culture medium (toxin peptide 11), preferably an antidote 9 to a poison, or a mutated target sequence that provides for the host cell resistance to a specific toxin, such as a bacteriocin, an antibiotic, a herbicide or a fungicide.

Preferably, the cassette sequence 2 further comprises between the first nucleotide sequence 3 and the second nucleotide sequences 5 and linked to them, a third nucleotide sequence 4, encoding for a linker peptide 8 having a length comprised between about 2 and about 500 amino acids, preferably between about 3, 4, 5, 6, 7, 8, 9, 10, 11, 12, 13, 14, 15, 20, 25, 30, 35, 40, 45, 50, 55 or 60 and about 500, 450, 400, 350, 300, 250, 200, 150 and 100 amino acids.

Advantageously, the length of the linker peptide 8 is adequate to allow that the conformational properties or sequence of the peptide or protein of interest 7 do not affect the activity of the second peptide 9, especially its antitoxin activity and its capacity to interact with the exogenous or endogenous toxin 11, 12 or 15 and block its toxic activity against the host cell 1. Preferably, the length of the linker peptide 8 is also sufficient, preferably having more than seven amino acids, to be cleavable by a peptidase.

Preferably, this linker peptide 8 is able to produce two peptides after cleavage, preferably being cleavable by addition of proteases, more preferably a Tobacco Etch Virus (TEV) protease.

Furthermore, the linker peptide 8 or the peptide or protein of interest 7, may include one or more sequences or modifications that encode specific sequences that are recognized by site-specific proteases to allow removal of the remaining portion or fragment, preferably a portion or the total sequence of the linker peptide 8.

A TEV protease is the common name for the 27 kDa catalytic domain of the Nuclear Inclusion a (NIa) protein encoded by the tobacco etch virus (TEV). Because its sequence specificity is far more stringent than that of the factor Xa, thrombin or enterokinase, TEV protease is a useful reagent for cleaving fusion proteins. TEV protease recognizes a linear epitope of the form E-Xaa-Xaa-Y-Xaa-Q-G/S with cleavage between the amino acid Q and amino acid G or amino acid Q and amino acid S. The most commonly used sequence is ENLYFQG.

Preferably, the linker peptide 8 is an intein able to produce two peptides after auto-catalytic self-cleavage.

Inteins are segments of proteins that are able to excise themselves and join the remaining portions "exteins" with a specific bond in a process termed protein splicing. Inteins are also called "protein introns". More particularly, an intein sequence that is located at the C-terminus of a protein of interest can excise itself spontaneously in the host cell, through a process known as "self-cleavage" (Cui et al. (2006) Prot. Expr. Purif. 50:74), resulting in two separate polypeptides:

the expected full-length recombinant protein (located N-terminus to this intein) and the C-terminal part of the polypeptide, (the intein itself, being possibly fused to a peptide with antitoxin activity)

Preferably, the linker peptide 8 is also able to produce two separate peptides upon translation by ribosome skipping or by STOPGO or STOP CARRY-ON. Instead of a fusion protein 10, ribosome skipping generates a first peptide comprising the peptide or protein of interest 7 and the N-terminal part of the linker peptide 8, and a second peptide comprising the C-terminal part of the linker peptide 8 and the antidote protein 9. More preferably the linker peptide 8 is a peptide from the 2A family.

The present invention is also related to a cloning kit, comprising suitable elements, preferably included in different vials, for performing the transformation or cloning step according to the invention, in particular the cassette sequence 2, or a cassette that only comprises the second nucleotide sequence 5 (encoding the antidote protein 9) or the second nucleotide sequence 5 and the third nucleotide sequence 4 (encoding the linker peptide 8), possibly with suitable restriction sites for cloning the first nucleotide sequence 3 immediately upstream the second nucleotide sequence 5 or immediately upstream the third nucleotide sequence 4, or the vector according to the invention and possibly a sufficient amount of the exogenous toxin peptide 11, which can be added to the culture medium of a cell 1 as represented in FIG. 1.

The kit according to the invention may also comprise this host cell 1 and the culture medium of this host cell 1.

Preferably, the host cell 1 to be transformed by the cassette sequence 2, or comprising the cassette sequence 2, may comprise in its genome, preferably in its chromosome, preferably under the control of a first controllable, inducible and/or repressible, promoter and/or operator sequence 14, one or more copies of a fourth nucleotide sequence 13 encoding (coding for) the toxin 12 or 15, i.e. a cytotoxin or a toxic compound to the host cell 1, more preferably a poison peptide, that is toxic, preferably lethal for the host cell 1, preferably this nucleotide sequence 13 is encoding the endogenous poison 15 secreted by the cell in its culture medium or the endogenous toxin 12 present in the cytoplasm of the cell.

As an alternative of the invention, the host cell 1 will not comprise in its genome any nucleotide sequence encoding this toxin, and the selection of the transformation step or survival control of the host cell is done by addition to the host cell culture medium of a sufficient amount of this toxin peptide 11 and/or a sufficient amount of a cell (which can be the host cell or a cell which is not the host cell) secreting in the culture medium, the toxin 15.

Examples of such exogenous or endogenous toxins 11, 12 or 15 that are toxic for the cell 1 are peptides, or other active compounds, reducing the growth of the cell by at least 50%, 60%, 70%, 80%, 90%, or being lethal and killing the host cell. Such toxin can also be a non-peptide compound preferably selected from the group consisting of a bacteriocin, an antibiotic, a herbicide, a fungicide or a mixture of antibiotics, herbicides or fungicides.

Other examples of "antitoxin sequence" include also mutated target sequences that provide for the host cells resistance to the activity of such specific non-peptide toxins, such as bacteriocins, antibiotics, herbicides or fungicides.

The first promoter and/or operator sequence 14 is preferably an inducible, or controllable, promoter and/or operator sequence, controllable by means well known to person skilled in the art, i.e. through temperature shift or addition of compound in the host cell culture medium, because it advantageously defines the level of production yield of the endogenous toxin 12 or 15 by the transformed host cell 1.

Preferably, the second nucleotide sequence 5 is the Kis sequence, or any other sequence preferably encoding a peptide or protein modified Kis, able to interact with Kid nucleotide sequence 13 or protein Kid 11, 12, 15 and avoiding its toxic lethal activity upon the host cell 1.

Alternatively, the second nucleotide sequence 5 can be any sequence that confers, to the transformed host cell 1, resistance to the toxic activity of a sufficient amount of the added exogenous toxin 11, such as for example an antibiotic or mixture of antibiotics, or an herbicide, especially if the host cell is plant cell, in the host cell 1 culture medium.

Advantageously, the host cell 1 transformed by the vector of the invention will generate after transcription and translation of the cassette sequence 2 present in the vector, the fusion protein 10 or two separate peptides (peptide 7 with the N-terminal part of linker peptide 8 and C-terminal part of linker peptide 8 with peptide 9) being produced by ribosome skipping. Preferably, this fusion protein 10 may include in its amino acid sequence, a linker peptide sequence 8 having a sufficient length of at least 2 amino acids preferably up to 500 amino acids or more.

Preferably, the linker peptide 8 is a functional peptide 2A, or any sequence generating two peptides from the translation of one ORF either by ribosome skipping, auto-cleavage or cleavage by site-specific proteases.

In the case of the cassette sequence 2 comprising a linker sequence 4 encoding a peptide 2A generates the formation of two different peptides:

the active antidote being antitoxin peptide or protein 9, covalently linked to its N-terminus to a first short peptide fragment or amino acid of the cleaved peptide 2A, or of a similar auto-cleavable peptide sequence, proline amino-acid from the cleaved portion or fragment of peptide 2A, or similar auto-cleavable protein, and, the peptide or protein of interest being the GFP protein 7, covalently linked to its C-terminus to the second portion of the cleaved peptide 2A, or of the cleavable portion of a similar auto-cleavable peptide.

Adequate means are also selected by the person skilled in the art for a purification of these two peptides, or proteins, and possibly a second specific cleaving of the remained portion of the linker peptide 8, preferably such as a portion of the peptide 2A sequence linked to the peptide or protein of interest 7.

This method compared to methods proposed in the state of the art will improved the production yield and quality of recombinant proteins, since this method and means require adequate production of protein fusion 10 or adequate production of antidote protein 9 by ribosome skipping, to counteract the toxic activity of the corresponding exogenous or endogenous toxin 11, 12 or 15, preferably the poison protein (Kid).

By the method and means of the invention, host cells possibly present in the bioreactor that do not produce the fusion protein 10 or the antidote protein 9 by ribosome skipping, will be killed by the activity of the corresponding exogenous or endogenous toxin 11, 12 or 15. This will avoid generation of heterogeneous host cell sub-populations producing non complete and possibly inactive proteins of interest or producing low amounts or no protein of interest 7. Therefore, with the method and means according to the invention, a high production and high qualitative yield of the recombinant peptide or protein of interest 7 as a fusion protein 10 (through a translational coupling) is obtained.

Indeed, any non-desired genetic modification, such as point mutation(s) (nucleotide(s) substitution(s)), deletion(s) or addition(s) of one or more nucleotide(s)), in the first sequence 3, the gene of interest, encoding the peptide or protein of interest 7, will result in altered production of the antidote protein 9 moiety of the fusion protein 10, quantitatively or qualitatively. Transcription errors (nucleotide(s) substitution(s), deletion(s) or addition(s) of one or more nucleotide(s), or premature arrest of transcription) resulting in altered expression of the peptide or protein of interest 7 moiety of the fusion protein 10, will also result in altered production of the antidote protein 9 moiety of the fusion protein 10, quantitatively or qualitatively. Translation errors (frameshifts, premature arrest of translation) resulting in altered expression of the peptide or protein of interest 7 moiety of the fusion protein 10, will also result in altered production of the antidote protein 9 moiety of the fusion protein 10, quantitatively or qualitatively. In addition, genetic mutations elsewhere in the genome of the host cell 1 (including chromosomal and extra-chromosomal elements) or transcriptional, post-transcriptional, translational, or post-translational errors during production of host cell constituents (proteins, RNAs, metabolites) can also directly or indirectly affect the transcription or translation of the peptide or protein of interest 7 moiety of the fusion protein 10, which will also result in altered production of the antidote protein 9 moiety of the fusion protein 10, quantitatively or qualitatively.

Consequently, any incorrect amino acid sequence of the antitoxin 9 present in the fusion protein is probably not able to antagonise to its corresponding exogenous or endogenous toxin 11, 12 or 15 and will result into the killing of the transformed cell 1 by the toxic activity of this toxin. Therefore, any host cell that is not producing correctly the peptide or protein of interest 7, but also any cell that is producing a modified peptide or protein of interest is advantageously and immediately killed from the host cell culture, preferably from the bioreactor comprising this host cell and therefore such cells will not consume the growth medium present in the bioreactor and will not produce the modified peptide or protein of interest. Consequently, only the host cells producing efficiently the unmodified protein of interest 7 included in the fusion protein 10 will be selected, will be able to grow and will remain in the bioreactor.

Example: Recombinant Protein Overexpression in Host Cells (Laboratory Protocol)

*Saccharomyces cerevisiae* cells contain plasmid A (pRS425-Met25 plasmid (Mumberg D, et al. Nucl. Acids Res. 22: 5767-5768, 1994) with the cassette integrated between XbaI and EcoRI restriction sites) and a second plasmid B (pRS416-GAL1 (Mumberg D, et al. Nucl. Acids Res. 22: 5767-5768, 1994) with the toxin sequence according to the invention and being integrated between XbaI and EcoRI restriction sites).

Media

Liquid Culture Medium a (1 Liter)
  Difco Yeast Nitrogen Base w/o amino acids (ref. 291920)
  Glucose 3% (final concentration)
  Methionine 500 uM (final concentration)
  Addition of water to adjust to 1 liter Liquid Culture Medium B (1 Liter)
  Difco Yeast Nitrogen Base w/o amino acids (ref. 291920)
  Galactose 3% (final concentration)
  Addition of water to adjust to 1 liter Procotol:

Day 0
  A culture cells bearing both plasmid A and B are present in liquid culture medium A from glycerol or isolated colony
  The dilution factor (knowing lag time and growth rate) to reach OD660 nm of 0.2 at DAY1 was calculated. According to this dilution factor, a dilution of the previous culture in the pre-warmed liquid medium A (50 ml in 250 ml Erlenmeyer flask) incubated at 30° C.; 160 RPM was obtained.

Day 1
  When $OD_{660\ nm}$ reached 0.2, the inventors have applied the following steps:
  Centrifugation of the culture at 3000 RPM for 2 minutes at 30° C.
  Removing of the supernatant
  Resuspension of the pellet in 50 ml of a pre-warmed culture medium B
  Centrifugation at 3000 RPM for 2 minutes at 30° C.
  Resuspension of the pellet in 50 ml of a pre-warmed culture medium B
  Incubation at 30° C.; before centrifugation at 160 RPM for 180 minutes (until $OD_{660\ nm}$ reaches 0.5).
  Centrifugation of the culture at 3000 RPM for 2 minutes at 4° C.
  Removing of the supernatant
  Finally the obtained pellet was subjected to high quality protein extraction.

```
Cassette sequence (composed of GFPmut2 sequence in
the same ORF with P2A sequence in the same ORF
with optimized kis antitoxin)
                                    (SEQ ID NO.: 15)
ATGAGTAAAGGAGAAGAACTTTTCACTGGAGTTGTCCCAATTCTTGTTGA

ATTAGATGGTGATGTTAATGGGCACAAATTTTCTGTCAGTGGAGAGGGTG

AAGGTGATGCAACATACGGAAAACTTACCCTTAAATTTATTTGCACTACT

GGAAAACTACCTGTTCCATGGCCAACACTTGTCACTACTTTCGCGTATGG

TCTTCAATGCTTTGCGAGATACCCAGATCATATGAAACAGCATGACTTTT

TCAAGAGTGCCATGCCCGAAGGTTATGTACAGGAAAGAACTATATTTTTC

AAAGATGACGGGAACTACAAGACACGTGCTGAAGTCAAGTTTGAAGGTGA

TACCCTTGTTAATAGAATCGAGTTAAAAGGTATTGATTTTAAAGAAGATG

GAAACATTCTTGGACACAAATTGGAATACAACTATAACTCACACAATGTA

TACATCATGGCAGACAAACAAAAGAATGGAATCAAAGTTAACTTCAAAAT
```

TAGACACAACATTGAAGATGGAAGCGTTCAACTAGCAGACCATTATCAAC

AAAATACTCCAATTGGCGATGGCCCTGTCCTTTTACCAGACAACCATTAC

CTGTCCACACAATCTGCCCTTTCGAAAGATCCCAACGAAAAGAGAGACCA

CATGGTCCTTCTTGAGTTTGTAACAGCTGCTGGGATTACCCATGGTATGG

ATGAATTGTACAAAGGAAGCGGAGCTACTAACTTCAGCCTGCTGAAGCAG

GCTGGAGACGTGGAGGAGAACCCTGGACCTCACACTACTAGATTGAAGAG

AGTTGGTGGTTCTGTTATGTTGACTGTTCCACCAGCTTTGTTGAACGCTT

TGTCTTTGGGTACTGACAACGAAGTTGGTATGGTTATTGACAACGGTAGA

TTGATTGTTGAACCATACAGAAGACCACAATACTCTTTGGCTGAATTGTT

GGCTCAATGTGACCCAAACGCTGAAATTTCTGCTGAAGAAAGAGAATGGT

TGGACGCTCCAGCTACTGGTCAAGAAGAAATTTAATAA.

Toxin sequence (Optimized kid toxin (from Kis/Kid
toxin-antitoxin system))
(SEQ ID NO.: 16)
ATGTTGAAGTACCAATTGAAGAACGAAAACGGTTGGATGCACAGAAGATT

GGTTAGAAGAAAGTCTGACATGGAAAGAGGTGAAATTTGGTTGGTTTCTT

TGGACCCAACTGCTGGTCACGAACAACAAGGTACTAGACCAGTTTTGATT

GTTACTCCAGCTGCTTTCAACAGAGTTACTAGATTGCCAGTTGTTGTTCC

AGTTACTTCTGGTGGTAACTTCGCTAGAACTGCTGGTTTCGCTGTTTCTT

TGGACGGTGTTGGTATTAGAACTACTGGTGTTGTTAGATGTGACCAACCA

AGAACTATTGACATGAAGGCTAGAGGTGGTAAGAGATTGGAAAGAGTTCC

AGAAACTATTATGAACGAAGTTTTGGGTAGATTGTCTACTATTTTGACTT

AATAA.

---

The invention claimed is:

1. A host cell comprising in its genome,
(i) a cassette sequence or a vector comprising said cassette sequence, wherein the cassette sequence or vector comprising said cassette sequence is expressed in said host cell, the cassette sequence comprising:
a first nucleotide sequence encoding a peptide of interest,
a second nucleotide sequence encoding an antitoxin peptide to a toxin, wherein the antitoxin peptide is only encoded within the host cell by this second nucleotide sequence, and
a third nucleotide sequence encoding a linker peptide having a length comprising between 2 and 500 amino acids;
wherein the first, second, and third nucleotide sequences are organized to encode a fusion protein comprising, from N- to C-terminal, the protein of interest, the linker peptide, and the antitoxin; and
(ii) one or more copies of a fourth nucleotide sequence encoding a toxin which is toxic to the host cell, wherein said fourth nucleotide sequence is expressed in said host cell.

2. The host cell of claim 1, wherein the linker peptide comprises a sequence cleavable by a protease.

3. The host cell of claim 2, wherein the protease is the TEV protease.

4. The host cell of claim 1, wherein the linker peptide is an auto-cleavable peptide.

5. The host cell of claim 1, wherein the toxin is an herbicide or fungicide.

6. The host cell of claim 1, wherein the toxin/antitoxin peptides that are expressed in said host cell are selected from the group consisting of CcdB/CcdA, Kid/Kis (PemK/PemI), ParE/ParD, MazE/MazF, RelE/RelB, YafO/YafN, HipA/HipB, Doc/PhD, VapCNapB, VapDNapX, HicA/HicB, YoeB/YefN, YafQ/DinJ, Tse2/Tsi2(PA2702/PA2703), TseI (PA1844)/TsiI, Tse3(PA3484)/Tsi3, C-terminal portions of Rhs (Rhs-CT) or CdiA (Cdi-CT) peptides/associated immune peptides RhsI or CdiI, or bacteriocins peptides.

7. The host cell of claim 6, wherein the toxin/antitoxin peptides are Kid/Kis peptides.

8. The host cell of claim 1, wherein the toxin is lethal for the host cell.

9. The host cell of claim 1, wherein the vector is a plasmid.

10. The host cell of claim 1, wherein the host cell is a bacterial cell.

11. The host cell of claim 10, wherein the bacterial cell is *E. coli*.

12. The host cell of claim 1, wherein the host cells is a eukaryotic cell.

13. A method for improving the expression of a peptide of interest, said method comprising:
culturing the host cell of claim 1 in culture medium under conditions in which the fusion protein comprising the peptide of interest is expressed.

14. The method of claim 13, said method further comprising recovering the fusion protein comprising the peptide of interest or the peptide of interest from the host cell or the culture medium.

* * * * *